(12) United States Patent
Leide et al.

(10) Patent No.: US 6,888,954 B2
(45) Date of Patent: May 3, 2005

(54) DEVICE AND METHOD FOR RECORDING IMAGES

(75) Inventors: Erland Leide, Helsingborg (SE); Nils Wihlborg, Helsingborg (SE); Håkan Wedelsbäck, Ångelholm (SE); Tomas Jonasson, Helsingborg (SE); Roger Ylikangas, Rydebäck (SE)

(73) Assignee: Foss Analytical AB, Hoganas (SE)

(*) Notice: Subject to any disclaimer, the term of this patent is extended or adjusted under 35 U.S.C. 154(b) by 716 days.

(21) Appl. No.: 09/757,696

(22) Filed: Jan. 11, 2001

(65) Prior Publication Data

US 2002/0061124 A1 May 23, 2002

(30) Foreign Application Priority Data

Nov. 17, 2000 (SE) ................................................ 0004235

(51) Int. Cl.⁷ .................................................. G06K 9/00
(52) U.S. Cl. ...................... 382/110; 382/165; 345/690; 348/68
(58) Field of Search ................................ 382/109, 110, 382/123, 143, 162, 164, 165, 168, 171, 173, 191, 203, 207, 274, 286, 305, 163, 166; 345/68, 92, 690, 581; 348/236, 453, 68, 92; 356/72, 239.7; 430/531; 250/341.7; 702/81; 428/35.8

(56) References Cited

U.S. PATENT DOCUMENTS

| | | | |
|---|---|---|---|
| 4,245,188 A | | 1/1981 | Rottmar |
| 5,245,188 A | * | 9/1993 | Satake et al. ............ 250/341.7 |
| 5,368,996 A | * | 11/1994 | Asami ........................ 430/531 |
| 5,641,596 A | * | 6/1997 | Gray et al. .................... 430/21 |
| 5,835,206 A | * | 11/1998 | Tragesser ..................... 356/72 |
| 5,956,413 A | * | 9/1999 | Oste et al. .................. 382/110 |
| 6,427,128 B1 | * | 7/2002 | Satake et al. ................. 702/81 |
| 6,610,378 B1 | * | 8/2003 | Kimura et al. ............. 428/35.8 |

FOREIGN PATENT DOCUMENTS

| | | |
|---|---|---|
| EP | 1 046 902 | 10/2000 |
| JP | 2 179452 | 7/1990 |
| JP | 9 292344 | 11/1997 |
| JP | 10 052673 | 2/1998 |
| JP | 10 309539 | 11/1998 |
| JP | 11 000621 | 1/1999 |
| JP | 2000 157936 | 6/2000 |

OTHER PUBLICATIONS

Gunansekaran et al., "Image Processing for Stress Cracks in Corn Kernels", St. Joseph, Michigan: American Society of Agricultural Engineers (ASAE), 1987, vol. 30, No.1, pp. 266–271.

* cited by examiner

Primary Examiner—Bhavesh M. Mehta
Assistant Examiner—Seyed Azarian
(74) Attorney, Agent, or Firm—Browdy and Neimark, P.L.L.C.

(57) ABSTRACT

A method for recording images of small particles to detect cracking includes feeding particle samples to a place for image recording, illumination a particle sample from at least two directions simultaneously, the illumination occurring with different light wavelengths for each direction, recording partial images of the illuminated particle in different channels, which are sensitive to different wavelengths, and comparing the different partial images to analyze the particle sample. Each partial image shows the particle sample illuminated from one direction by the channel recording only one of the different light wavelengths.

27 Claims, 4 Drawing Sheets

DEVICE AND METHOD FOR RECORDING IMAGES

FIELD OF THE INVENTION

The present invention relates to a method and a device for recording images of small particles, such as grains from cereals and like crops, to analyze the quality of the particles, especially to detect any cracking in the particles.

BACKGROUND ART

Inspection of different kinds of cereals and other crops is today made all over the world to determine the quality of the cereals in commercial transactions and handling. The inspection aims at examining a selected representative sample from a large consignment and determining the presence of non-desirable grains and particles. The non-approved grains and particles are classified and the quantity of each class is determined. Owing to the distribution of the various grains, the sample and, thus, the consignment will be given a grading which is a decisive factor in connection with payment and handling of the consignment.

Today most cereal inspections are carried out entirely manually. A skilled inspector has often passed through a comprehensive education of many years. Nevertheless there are great deviations in the analyses/classifications between different inspectors owing to, among other things, personal assessments and varying conditions of lighting. Deviations also occur in each individual inspector because of, for example, the degree of fatigue.

It is particularly difficult to detect cracking in the grains. A special problem is to detect cracks in rice. An inspector cannot detect cracked grains with the naked eye. Cracked grains can be detected by grains being placed on a sheet of glass with an inclined mirror underneath. When the grain is illuminated from above, cracks can be detected when looking at the grain in the mirror. According to another method, cracks can be detected if the grain is placed on a shimmering blue layout table. The inspector can then detect cracks by looking at the grain from different angles. Both methods imply that the inspector must be assisted by special illumination and place the grains so that they are correctly illuminated. This means that the analyzing process is slowed down significantly since the analysis of each grain takes a long time.

It is desirable for the analysis of grains to be automated in order to reduce the deviations and create a more stable situation involving a more transparent grading process. This means that a reliable method of detecting cracks in grains in an automated manner is needed. There is today no satisfactory method of detecting cracks, which means that an inspector still has an important role.

SUMMARY OF THE INVENTION

The object of the present invention is to provide automated detection of internal damage in particles, such as grains from cereals. A specific object is to provide detection of cracks, which is rapid and reliable.

The object of the invention is achieved by a method according to claim 1 and a device according to claim 15. Further advantages of the invention are evident from dependent claims 2–14 and 16–27.

Thus, the invention provides a method for recording images of small particles, such as grains from cereals and like crops, to analyze the quality of the particles, especially to detect any cracking in the particles. The method comprises the steps of feeding particle samples which each comprise at least one particle, to a place for recording an image, illuminating a particle sample from at least two directions simultaneously, the illumination occurring with different light wavelength for each direction, recording an image of the illuminated particle sample with the aid of an image-recording means, which records partial images of the particle sample in different channels, which are sensitive to different wavelengths, and comparing the different partial images for analysis of the particle sample Each partial image shows the particle sample illuminated from one direction by the channel recording only one of the different light wavelengths.

The invention is thus based on the understanding that it is possible to use the fact that image-recording means which can record color images record different light wavelengths in different channels in order to put them together to one color image. By illuminating a particle with different wavelengths from different directions, it appears to an individual channel as if the particle is illuminated from only one direction with one wavelength. Thus, simultaneous detection of illumination of the particle from different directions separately is obtained by the information in the channels being used separately and not in a put-together color image. The optical coupling between both sides of a crack or some other internal damage in the particle is inferior to that through an undamaged particle. This difference is reinforced by comparing the partial images, thus making it possible to compare the illumination from different sides of the crack.

The illumination and image recording of a particle sample occur preferably from angles to the particle sample which are so different that essentially no directly reflected light from the particle sample reaches the image-recording means. As a result, the major part of the light which is detected in the image-recording means is diffuse light. The diffuse light has been scattered inside a particle before it reaches the image-recording means. A crack, if any, may affect the diffuse light whereas directly reflected light does not have any effect at all. By the image-recording means mainly detecting diffuse light, the contrasts from a crack will appear more clearly.

The particle sample is advantageously illuminated with sweep light, i.e. the illumination occurs with sweeping incidence on the particle sample, and the angle of incidence of the light is close to 90° to the direction of the image-recording means. This minimizes the directly reflected light in the image-recording means. This means that the difference in optical coupling between both sides of the crack appears more clearly since the light must be scattered in the particle in order to reach the image-recording means.

According to a preferred embodiment, the particle samples are fed during continuous movement. This means that a minimum wear on mechanical parts arises owing to many retardations and accelerations of the particle samples.

The method suitably comprises the step of dividing an image of a particle sample comprising a plurality of particles into images of one particle each. As a result, a plurality of particles can be analyzed from one image. The method will not be dependent on the condition that only one particle at a time is always fed to the image-recording.

Preferably, light transmitted through the particle sample is measured in the image-recording means. This means that the light is scattered many times in the particle before it reaches the image-recording means. This accentuates the effects of a crack.

According to a preferred embodiment, only one particle is fed in each particle sample. This means that a physical separation of the particles is obtained. In a plurality of analyses of the same particle using different illumination techniques, a physical separation is preferred.

The particle samples are advantageously fed by a carrier which has sample holders for taking up one particle in each sample holder, which are formed like the particles so that the orientation of a particle in the sample holder is controlled. This means that the particles can be oriented so as to fill the image that is being recorded as much as possible since one long side of the particle can be adapted to follow one long side of the image. That the orientation of the particles is known is also an advantage in case of e.g. grains of rice, by the cracks in most cases having the same direction in the grain. The direction of a possible crack is thus known, which facilitates illumination and detection.

The particle sample is suitably illuminated with two different wavelengths from two different illuminating means, and the angle between the directions of illumination of the two illuminating means is essentially 180°.

In this context use is made of the fact that cracks in, for instance, grains of rice are usually oriented transversely of the grain. Since the orientation of the grain can be determined, it is thus possible to illuminate the grain from its short sides, which means that the light is incident perpendicularly on the crack. This makes the effect of the low optical coupling between the two sides of the crack appear clearly.

In another embodiment, the particle sample is illuminated with three different wavelengths from three different illuminating means, and the angle of the directions of illumination of two neighboring illuminating means is essentially 120°. This embodiment is convenient to use when the orientation of the particles is not known and/or when the orientation of the cracks in the particles can vary significantly. As a result, the particle is illuminated from three clearly separated directions and the optical effect of the crack is accentuated when comparing the two partial images that have been recorded with incident light which is closest to be perpendicular to the crack.

The step of comparing the different partial images comprises preferably the step of subtracting the partial image from a first channel from the partial image from a second channel. This subtraction of one partial image from another means that the effects of a crack in the particle are reinforced since one partial image comprises the particle illuminated from one side of the crack and the other partial image comprises the particle illuminated from the other side of the crack. Therefore the effect of the crack will be doubled and appear more clearly.

The image-recording means is advantageously a digital camera. A digital camera is relatively quick and produces an image in digital format, which is convenient for the image to be automatically analyzed.

The method comprises in a preferred embodiment the step of following the feeding of the particle sample with a mirror, so that a mirror image of the particle sample falls on a center axis of the feeding movement, the mirror image of the particle sample standing essentially still seen from the image-recording means as image recording occurs, owing to the fact that the mirror image of the particle sample is positioned on the center axis of the movement.

In this way, particles can be fed at high speed past the image-recording means. Movement blur will not arise even if the image-recording means does not have an extremely short time of exposure since the particle appears to stand still in the mirror, seen from the image-recording means. By the image mirror essentially standing still is meant that no translational movement occurs but only a small degree of rotation owing to the movement of the mirror in front of the detector. This movement of rotation, however, is so small that no movement blur arises. Furthermore, a relatively long time of exposure means that the quantities of light need not be very large.

The different light wavelengths comprise preferably red, green and blue light. This is suitable since it is common in digital cameras, such as CCD cameras, that color images are recorded by precisely red, green and blue light being recorded in different channels.

The object of the invention is also achieved by a device for recording images of small particles, such as grains from cereals and like crops, to analyze the quality of the particles, especially to detect any cracking in the particles. The device comprises a carrier which feeds particle samples which each comprise at least one particle to a place for image recording, at least two illuminating means which are adapted to simultaneously illuminate a particle sample with different light wavelength and from different directions, an image-recording means which records an image of the illuminated particle sample, the image-recording means recording partial images of the particle sample in different channels which are sensitive to different wavelengths, and an analyzing means for comparing the different partial images for analysis of the particle sample. Each partial image shows the partial sample illuminated from one direction by the channel recording only one of the different light wavelengths.

By the image-recording means recording different light wavelengths in different channels, simultaneous detection of illumination of a particle can be made separately from a plurality of directions. The illumination thus occurs with different wavelengths from different directions and a channel recognizes the particle as being illuminated from one direction only. By the image recording of the illumination from different directions occurring simultaneously, the particle need not be oriented in exactly the same manner in different measurements for comparisons to be made. The need for the particle to be oriented in the same way could also be obviated by the particle lying still in front of the image-recording means between measurements. The inventive device now permits much quicker feeding of particles than if the particle had to lie still in front of the image-recording means for a plurality of measurements.

BRIEF DESCRIPTION OF THE DRAWINGS

A presently preferred embodiment of the invention will now be described by way of example with reference to the accompanying drawings.

DETAILED DESCRIPTION OF A PREFERRED EMBODIMENT

Figure 1:
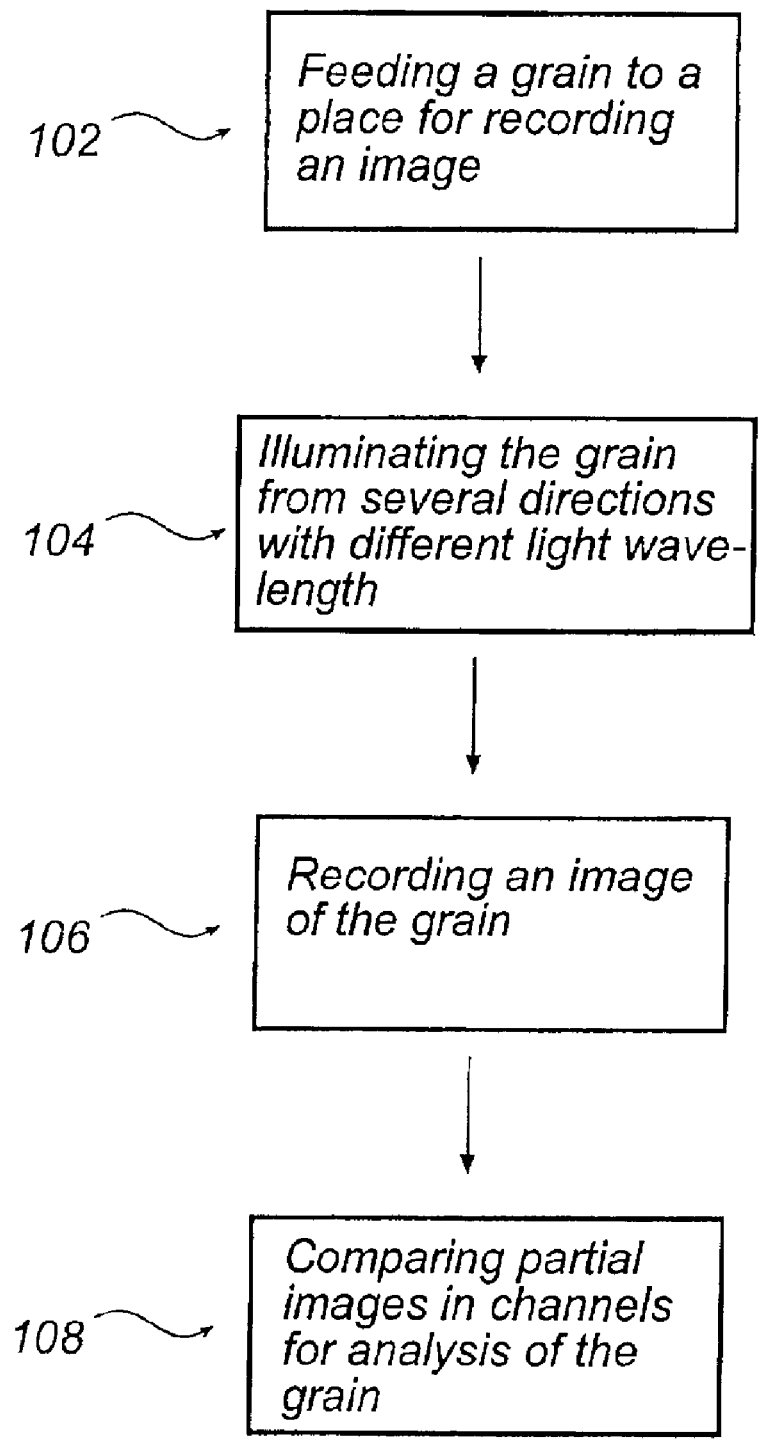
FIG. 1 is a block diagram and describes the method according to the invention.

A method according to the invention for detecting cracks or other internal damage in cereals, such as rice or other transparent or semitransparent particles, will now be described in more detail with reference to FIG. 1.

A representative sample is taken from a large volume that is to be analyzed. The sample consists in most cases of about 1200 grains or particles (about 30 g) but can be up to 150 g. The sample is inserted into an instrument for analysis. There the particles are separated physically for analysis to be made of one particle at a time. The physical separation occurs in some conventional manner. The separated particle is then fed, step 102, to a place for image recording. Here the particle is illuminated with sweep light, step 104, i.e. the angle of incidence of the light to the normal of the particle is close to 90° and the light is almost tangent to the particle.

Illumination takes place from several directions, with different light wavelengths from each direction. The light will be scattered in the particle several times before it is emitted as diffusely reflected or diffusely transmitted light. An image-recording means is adapted to record an image of the particle straight from above. This image thus comprises above all information about the diffuse light. Directly reflected light does not reach the image-recording means since the angle of deflection of the light from the particle corresponds to the angle of incidence of the light on the particle, and the image-recording means records light with a small angle of deflection. Directly transmitted light, i.e. light that has not been scattered in the particle, constitutes a very small part of the transmitted light owing to the very small probability that light should pass through a solid medium without being scattered. Preferably, transmitted light is detected since this means greater scattering of the light before it is detected. When detecting transmitted light, the angle of incidence of the light on the particle is not equally important, but also in this case it may be advantageous to illuminate the particle with sweep light.

Cracking in the particle causes deteriorated optical coupling between the two sides of the crack. This means that light that has struck one side of the crack will, to a very small extent, be transmitted to the other side of the crack. Therefore a great difference in light intensity on the different sides of the crack will be seen. For a crack in the particle to appear clearly, the incident light should be perpendicular to the crack. At least the light should be incident mainly, and preferably only, on one side of the crack in the particle.

The particle is illuminated by three sources of light with an angle of 120° between two neighboring sources of light. Consequently it will be possible to ensure in an optimal manner that the light from a pair of the sources of light is incident on one side each of the crack. If the direction of the crack is known in the particle, this can be used by illuminating the particle from one side each of the crack with an angle of 180° between the sources of light. It goes without saying that this results in a better contrast but thus requires that the direction of the crack and the orientation of the particle be known.

An image of the illuminated particle is recorded, step 106, in the image-recording means. The illumination from an individual direction is detected in a channel of its own by the channel being merely sensitive to the light wavelength of the light from the individual direction. The information in a channel is recorded in the image-recording means in the form of a partial image. The image-recording means is a conventional digital camera, such as a CCD camera, which records red, green and blue light as partial images in different channels. Therefore the illumination occurs with red, green and blue light in the three sources of light to fit the sensitivity of the channels of the camera. If only two sources of light are used when the orientation of the crack is known, red and blue light are used since these wavelengths differ most.

The partial images are normally used to put together a color image by the intensity relationship between a number of colors being determined for each pixel in the image. Instead, here use is made of each partial image as an image of the illumination of a particle from one direction. These partial images can then be compared, step 108, to reinforce the effects of a crack. The reinforcement of the effects occurs by one partial image being subtracted from another. If these partial images contain information about illumination of the particle from one side each of a crack, the effect of the crack will be doubled in the resulting image. After reinforcement of the effect, an image analysis is carried out to check whether there is a clear dividing line that defines areas in the particle with a great difference in light intensity. If there is such a dividing line, this indicates that there is a crack in the particle and the particle is classified as cracked.

Figure 2:
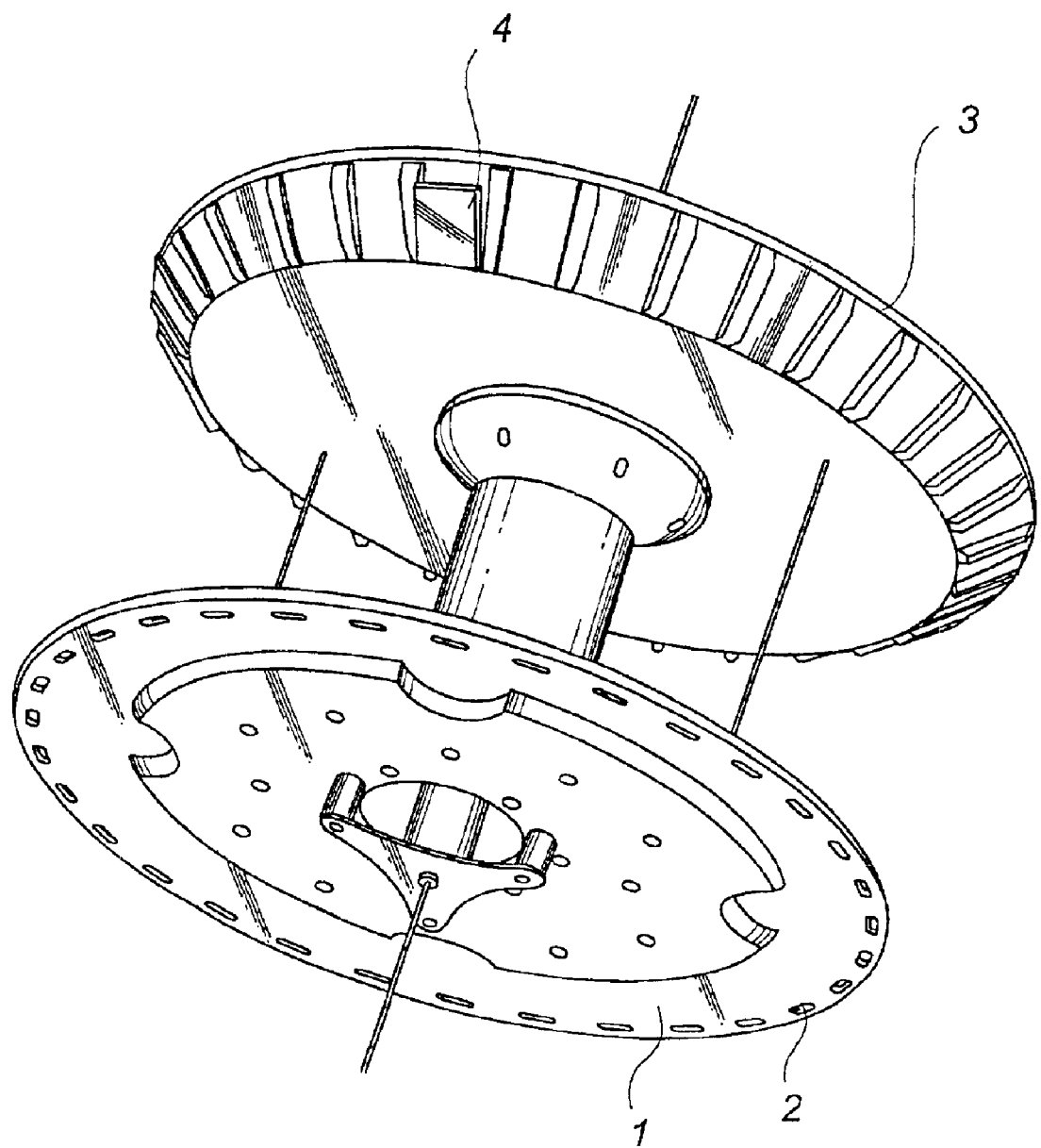
FIG. 2 is a perspective view of a sample-feeding carrier for feeding particle samples to a place for recording images.

A device, in which the method above is carried out, will now be described in more detail with reference to FIG. 2. The device has a carrier 1, which is adapted to feed particles to a place where illumination and image recording of the particles take place. The carrier 1 is a disk which has sample holders 2 along the periphery of the disk. A sample holder 2 consists of a hole which takes up a particle. The carrier 1 is rotated inside a stand and, by rotation, particles are fed continuously by sample holders 2 to a place for image recording. The carrier need, of course, not rotate during continuous movement. A continuous movement, however, causes little wear on mechanical parts and is therefore preferred.

The particles can be made to adhere by suction to the sample holders 2 by a subatmospheric pressure being generated on the underside of the carrier 1. The holes are so small that only one particle at a time can adhere and no particle can fall through a hole. The orientation of the particle on the carrier 1 can in this case be arbitrary and, thus, three illuminating means should be used as discussed above. These illuminating means are fixedly mounted on the stand with an angle of 120° between two neighboring illuminating means. In this position, also an image-recording means is mounted on the stand. Here the particle is illuminated with illuminating means and an image of the illuminated particle is recorded by the image-recording means as described above.

The sample holders 2 can, according to another embodiment, consist of particle-shaped holes. The carrier 1 then rotates on top of a particle holding disk which thus constitutes a bottom of the holes. A particle thus falls down in a hole and fits the hole in one way only, thereby making it possible to control the orientation of the particle. As the carrier 1 rotates the particle is then advanced on the particle holding disk. Since the orientation of the particle is known, knowledge of the normal orientation of the cracks in the particle can be utilized. For grains of rice, for instance, cracks are oriented transversely of the elongate direction of the grain. As a result, the grain can be illuminated from its short sides and the light will be incident perpendicularly on a crack, if any, in the grain. Two light-emitting diodes, one red and one blue, are thus mounted in the opposite short side walls of each sample holder 2.

The partial images that are recorded in the image-recording means are sent as input data to calculation circuits in the instrument. These carry out an image analysis for subtraction between two partial images of a particle and determining whether a dividing line which marks a crack is to be found in the particle.

A mirror-supporting means 3 is arranged to follow the movements of the carrier 1. The mirror-supporting means 3 has for each sample holder 2 a corresponding mirror 4. The mirror 4 projects a particle in the sample holder 2 on a center axis of the movement. This means that the image-recording means which records an image of the mirror image of the particle perceives that the particle stands still in the mirror. The mirror image of the particle is all the time on the center axis, and the only movement in the mirror image is a turning about the center of the particle. The degree of this turning corresponds to the angle through which the mirror-supporting means 3 is turned while a mirror 4 is positioned in front of the image-recording means. This turning is so small that no or very little movement blur arises in the recorded image. This device makes it possible for the image-recording means to have a relatively long time of exposure, which can be managed by a conventional digital camera.

Figure 3:
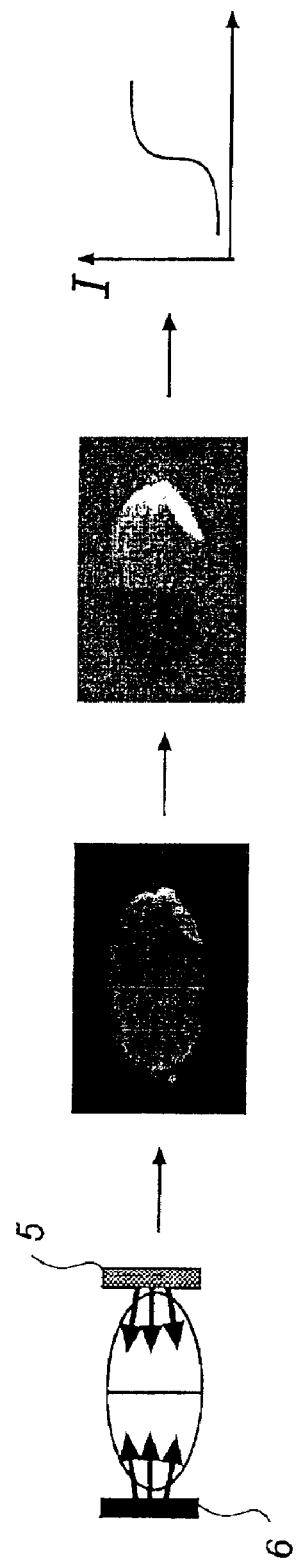
FIG. 3 illustrates schematically illumination of a grain of rice from two opposite directions according to one embodiment of the invention.
Figure 4:
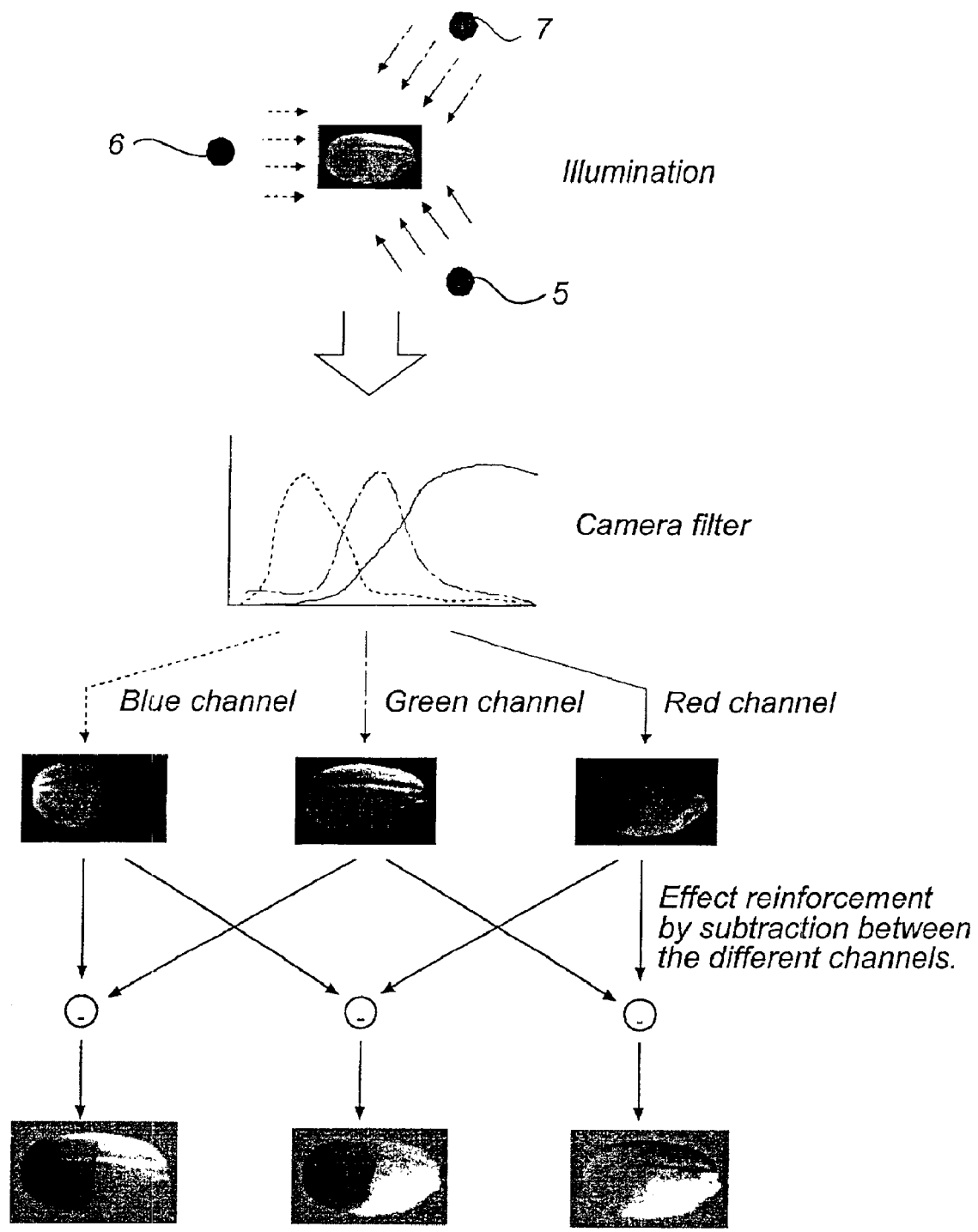
FIG. 4 illustrates schematically illumination of a grain of rice from three different directions according to another embodiment of the invention.

FIGS. 3 and 4 illustrate schematically how the image analysis occurs in connection with illumination from two (FIG. 3) and three (FIG. 4) directions. In FIG. 3, both the red light 5 and the blue light 6 are incident perpendicularly on the crack, and the distinct difference in contrast is clearly to be seen after subtraction of the blue channel from the red. In FIG. 4, the blue light 6 is perpendicular to the crack while the green light 7 and the red light 5 do not accentuate the crack in the same clear manner. After reinforcing the effect by subtraction of two channels at a time, it is, however, to be seen that the crack is clearly accentuated when comparing the blue and the green channel and, respectively, when comparing the blue and the red channel.

It will be appreciated that a large number of modifications of the embodiment described above are feasible within the scope of the invention as defined by the appended claims. For instance, other wavelengths can be used for the light, which means that the channels of the image-recording means in that case are sensitive to these wavelengths.

According to another alternative embodiment, a plurality of particles in a particle sample can be fed simultaneously to the place for image recording. The image of the illuminated particle sample can then be divided into a plurality of images of one particle each. These images can then be analyzed as usual. In this manner, a plurality of particles will be measured simultaneously, but some extra image processing is required.

The illuminating means can, of course, be any kind of light source which emits light with limited spectral contents, such as some sort of laser or a gas discharge lamp. The light source need not be limited to emitting a narrow ray of light but can emit light in a wide angle, but the illumination of the particle should, as mentioned above, be incident on one side only of a crack in the particle.

The image-recording means could be some other type of digital camera, such as a CMOS camera.

The invention is not limited to the detection of cracks in particles. Other kinds of internal damage can also be detected, such as insect damage, where an insect has bored a channel in the particle.

What we claim and desire to secure by Letters Patent is:

1. A method for recording images of small particles, to analyze the quality of the particles, especially to detect any cracking in the particles, said method comprising the steps of
   feeding particle samples which each comprise at least one particle, to a place for recording an image,
   illuminating a particle sample from at least two directions simultaneously, the illumination occurring with different light wavelength for each direction,
   recording an image of the illuminated particle sample with the aid of an image-recording means, which records partial images of the particle sample in different channels, which are sensitive to different wavelengths, and
   comparing the different partial images for analysis of the particle sample, each partial image showing the particle sample illuminated from one direction by the channel recording only one of the different light wavelengths.

2. The method as claimed in claim 1, wherein the illumination and recording of an image of a particle sample occur from angles to the particle sample which are so different that essentially no directly reflected light from the particle sample reaches the image-recording means.

3. The method as claimed in claim 2, wherein the particle sample is illuminated with sweep light, i.e. the illumination occurs with sweeping incidence on the particle sample, and the angle of incidence of the light is close to 900 to the direction of the image-recording means.

4. The method as claimed in claim 1, wherein the particle samples are fed during continuous movement.

5. The method as claimed in claim 1, further comprising the step of dividing an image of a particle sample comprising a plurality of particles, into images of one particle each.

6. The method as claimed in claim 1, wherein light transmitted through the particle sample is measured in the image-recording means.

7. The method as claimed in claim 1, wherein only one particle is fed in each particle sample.

8. The method as claimed in claim 7, wherein the particle samples are fed by a carrier, which has sample holders for taking up a particle in each sample holder, which are formed like the particles so that the orientation of a particle in the sample holder is controlled.

9. The method as claimed in claim 8, wherein the particle sample is illuminated with two different wavelengths from two different illuminating means and the angle between the directions of illumination of the two illuminating means is essentially 180°.

10. The method as claimed in claim 1, wherein the particle sample is illuminated with three different wavelengths from three different illuminating means, and the angle between the directions of illumination of two neighboring illuminating means is essentially 1200.

11. A method for recording images of small particles, to analyze the quality of the particles, especially to detect any cracking in the particles, said method comprising the steps of:
    feeding particle samples which each comprise at least one particle, to a place for recording an image,
    illuminating a particle sample from at least two directions simultaneously, the illumination occurring with different light wavelength for each direction,
    recording an image of the illuminated particle sample with the aid of an image-recording means, which records partial images of the particle sample in different channels, which are sensitive to different wavelengths, and
    comparing the different partial images for analysis of the particle sample, each partial image showing the particle sample illuminated from one direction by the channel recording only one of the different light wavelengths, wherein the step of comparing the different partial images comprises the, step of subtracting the partial image from a first channel from the partial image from a second channel.

12. The method as claimed in claim 1, wherein the image-recording means is a digital camera.

13. The method as claimed in claim 1, further comprising the step of following the feeding of the particle sample with a mirror, so that a mirror image of particle sample falls on a center axis of the feeding movement, the mirror image of the particle sample standing essentially still seen from the image-recording means as an image is being recorded, owing to the fact that the mirror image of the particle sample is positioned on the center axis of the movement.

14. The method as claimed in claim 1, wherein the different light wavelengths comprise red, green and blue light.

15. A device for recording images of small particles, to analyze the quality of the particles, especially to detect any cracking in the particles, said device comprising a carrier which feeds particle samples which each comprise at least one particle, to a place for image recording, at least two illuminating means which are adapted to simultaneously illuminate a particle sample with different light wavelength and from different directions, an image-recording means which records an image of the illuminated particle sample, the image-recording means recording partial images of the particle sample in different channels which are sensitive to different wavelengths, and an analyzing means for comparing the different partial images for analysis of the particle sample, each partial image showing the particle sample illuminated from one direction by the channel recording only one of the different light wavelengths.

16. The device as claimed in claim 15, wherein the illuminating means and the image-recording means are mounted at angles to the particle sample that are so different that essentially no directly reflected light from the particle sample reaches the image-recording means.

17. The device as claimed in claim 16, wherein the particle sample is illuminated with sweep light, i.e. illumination occurs with sweeping incidence on the particle sample, and the angle of incidence of the light is close to 900 to the direction of the image-recording means.

18. The device as claimed in claim 15, wherein the carrier is adapted to feed particle samples during continuous movement.

19. The device as claimed in claim 15, which comprises a means for image analysis of the recorded image, an image of a particle sample comprising a plurality of particles being, with the aid of the means for image analysis, divisible into images of one particle each.

20. The device as claimed in claim 15, wherein the illuminating means and the image-recording means are mounted on one side each of the particle sample, so that light transmitted through the particle sample is measured in the image-recording means.

21. The device as claimed in claim 15, wherein the carrier is adapted to take up only one particle in each particle sample.

22. The device as claimed in claim 21, wherein the carrier has sample holders for taking up one particle in each sample holder, which are formed like the particles so that the orientation of a particle in the sample holder is controlled.

23. The device as claimed in claim 22, wherein two different illuminating means are arranged on one side each of the sample holder, the angle between the directions of illumination of the two illuminating means being essentially 1800.

24. The device as claimed in claim 15, wherein three different illuminating means are arranged to illuminate the particle sample, the angle between the directions of illumination of two neighboring illuminating means being essentially 1200.

25. A method for recording images of small particles, to analyze the quality of the particles, especially to detect any cracking in the particles, said method comprising the steps of:

feeding particle samples which each comprise at least one particle, to a place for recording an image, illuminating a particle sample from at least two directions simultaneously, the illumination occurring with different light wavelength for each direction, recording an image of the illuminated particle sample with the aid of an image-recording means, which records partial images of the particle sample in different channels, which are sensitive to different wavelengths, and comparing the different partial images for analysis of the particle sample, each partial image showing the particle sample illuminated from one direction by the channel recording only one of the different light wavelengths, wherein the analyzing means is adapted to subtract the partial image from a first channel from the partial image from a second channel.

26. The device as claimed in claim 15, wherein the image-recording means is a digital camera.

27. The device as claimed in claim 22, further comprising an image-supporting means which has a mirror for each sample holder and following the movement of the sample holder and projecting a mirror image of a particle sample in the sample holder on a center axis of the feeding movement, the mirror image of the particle sample standing essentially still seen from the image-recording means as image recording occurs, owing to the fact that the mirror image of the particle sample is positioned on the center axis of the movement.

* * * * *